United States Patent [19]
Rost et al.

[11] Patent Number: 6,139,540
[45] Date of Patent: Oct. 31, 2000

[54] GUIDEWIRE WITH DISPOSITION TO COIL

[75] Inventors: Michael C. Rost, Souix Falls, S. Dak.;
Daniel L. Gabrielson, Maple Grove, Minn.

[73] Assignee: Lake Region Manufacturing, Inc., Chaska, Minn.

[21] Appl. No.: 08/961,366

[22] Filed: Oct. 30, 1997

[51] Int. Cl.[7] ................................................. A61M 27/00
[52] U.S. Cl. .............................. 604/585; 604/95; 604/96; 604/280; 604/281
[58] Field of Search ..................... 600/585, 933, 600/434; 604/95, 96, 280, 281, 282

[56] References Cited

U.S. PATENT DOCUMENTS

| | | | |
|---|---|---|---|
| Re. 34,695 | 8/1994 | Mar et al. . | |
| 4,582,181 | 4/1986 | Samson | 606/194 |
| 4,650,472 | 3/1987 | Bates . | |
| 4,655,750 | 4/1987 | Vaillancourt . | |
| 4,846,186 | 7/1989 | Box et al. | 600/585 |
| 5,084,022 | 1/1992 | Claude . | |
| 5,117,838 | 6/1992 | Palmer et al. . | |
| 5,221,269 | 6/1993 | Miller et al. | 604/281 |
| 5,251,640 | 10/1993 | Osborne | 600/585 |
| 5,279,573 | 1/1994 | Klosterman . | |
| 5,290,244 | 3/1994 | Moonka . | |
| 5,357,978 | 10/1994 | Turk . | |
| 5,358,495 | 10/1994 | Lynn . | |
| 5,392,918 | 2/1995 | Harrison . | |
| 5,443,081 | 8/1995 | Klosterman . | |
| 5,664,580 | 9/1997 | Erickson et al. . | |
| 5,666,968 | 9/1997 | Imran et al. | 600/585 |
| 5,722,425 | 3/1998 | Bostrom | 600/585 |
| 5,944,701 | 8/1999 | Dubrol | 600/585 |

*Primary Examiner*—Cary O'Connor
*Assistant Examiner*—Pamela Wingood
*Attorney, Agent, or Firm*—Michael Best & Friedrich LLP; Grady J. Frenchick, Esq.

[57] ABSTRACT

Guidewires having a substantially permanent disposition or predispostion to assume the configuration of a coil are disclosed. The guidewire assumes a coiled configuration when not in use and a straight or substantially linear configuration when being used to place a medical device within the anatomy of a patient. Guidewires of invention advantageously reduces the likelihood that the guidewire will fall out of the sterile field during a medical procedure and become contaminated, requiring replacement. Methods for making the guidewire also are disclosed.

15 Claims, 9 Drawing Sheets

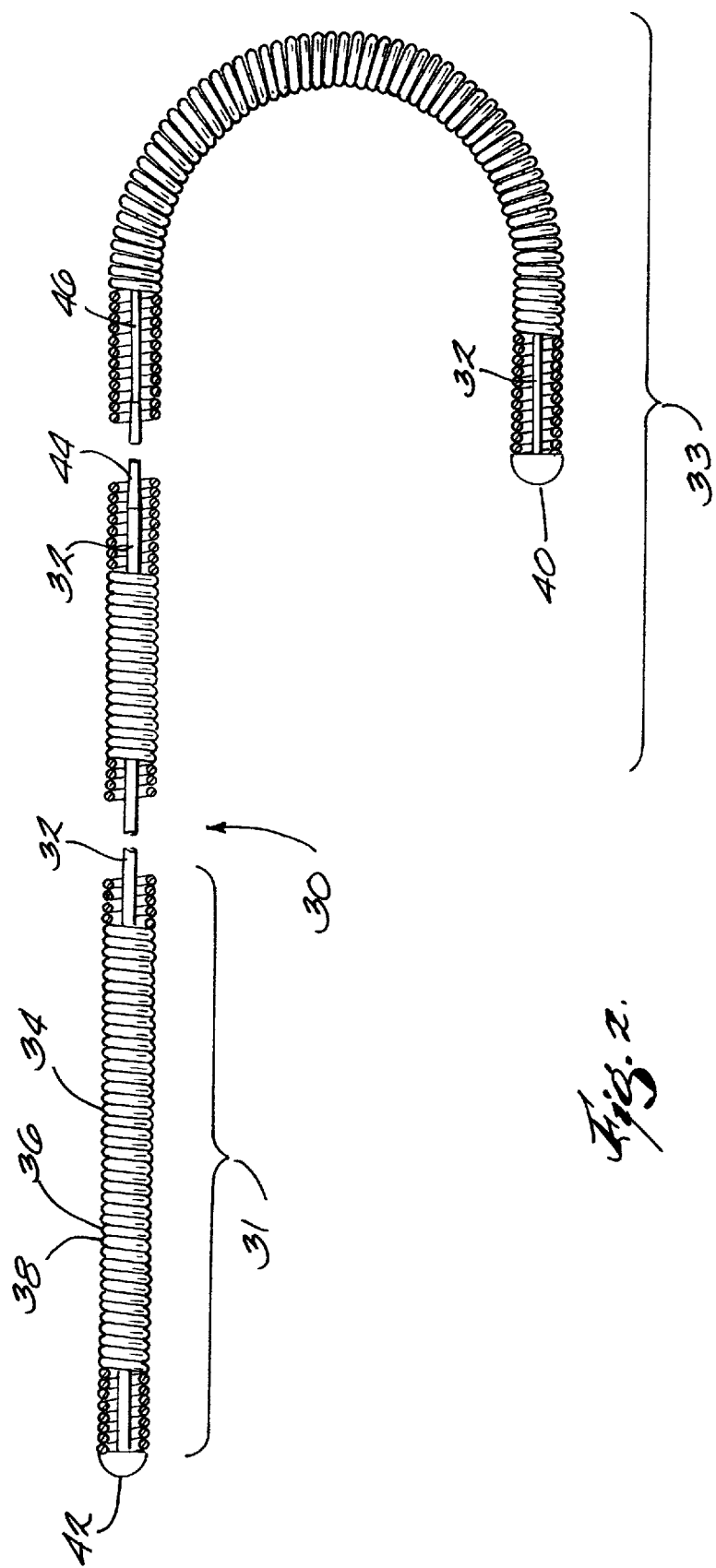

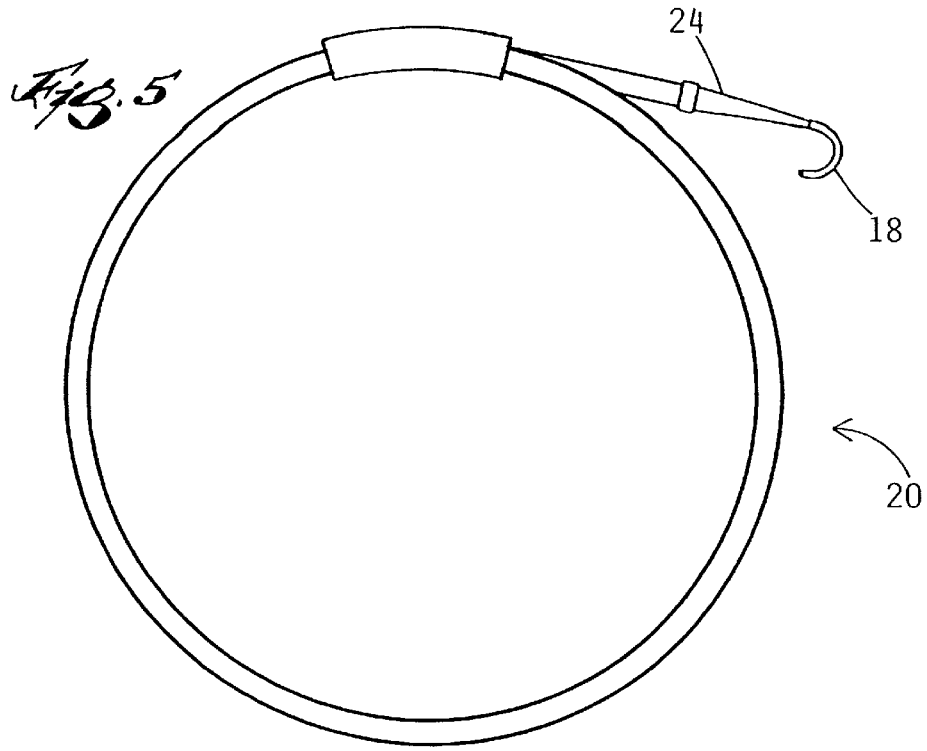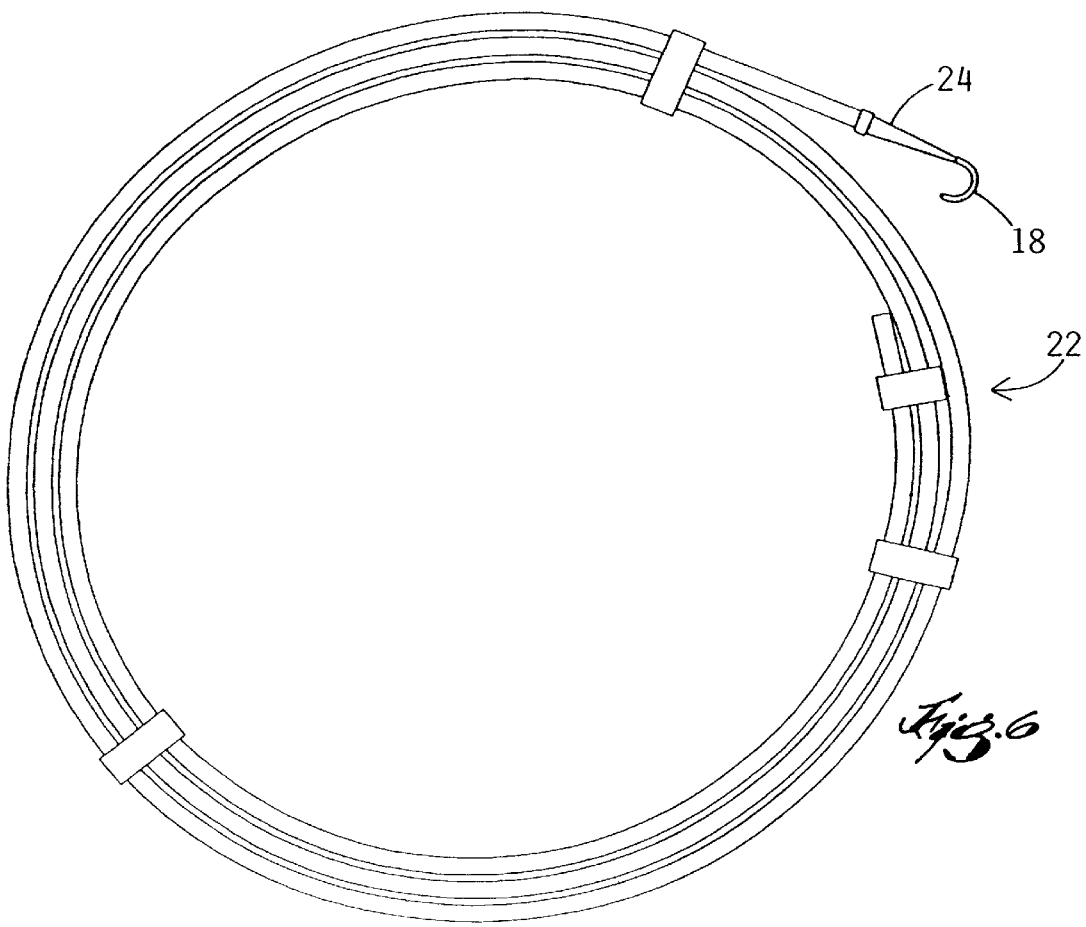

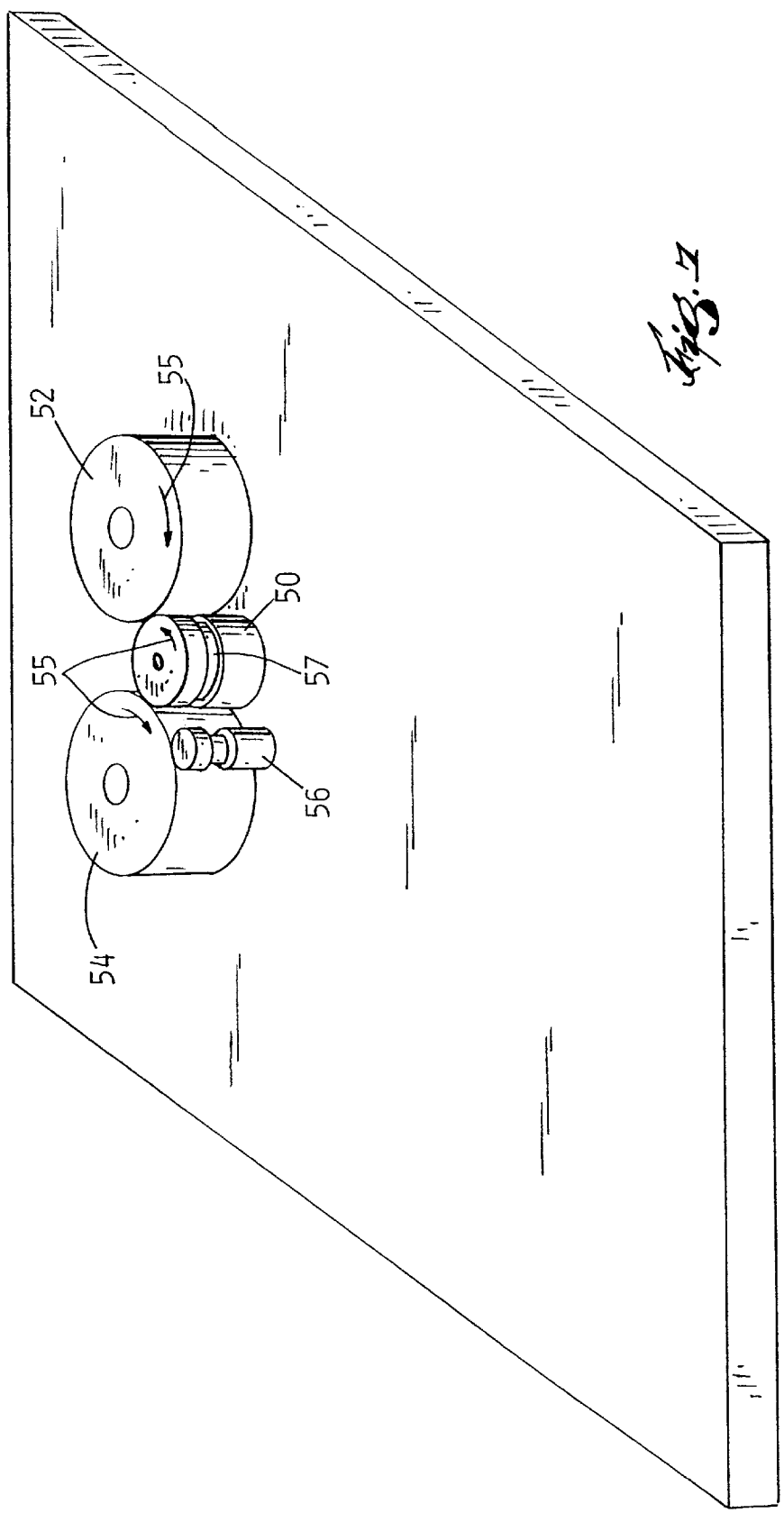

GUIDEWIRE WITH DISPOSITION TO COIL

CROSS-REFERENCE TO RELATED APPLICATIONS

Not Applicable

BACKGROUND OF THE INVENTION

This invention relates to the field of guidewires or wire guides used for diagnostic, interventional, or therapeutic medical procedures which define and are carried out within a sterile field. More specifically, this invention relates to guidewires which are conveniently useable within the spatial limits of a sterile field. Guidewires of this invention also significantly reduce the likelihood that they will become contaminated by physical displacement from the sterile field or inadvertent contact with a non-sterile surface.

Guidewires are used in various medical procedures to gain vascular or non-vascular access to anatomical locations. The guidewire is initially introduced into the anatomy of a patient by means of a needle or other access device which in many procedures pierces the patient's skin. The guidewire is then advanced to a chosen or targeted anatomical location to provide a means of tracking guidance and support for other diagnostic, interventional, or therapeutic medical devices having lumens which can follow or track over a guidewire. Once such other medical devices reach their desired anatomical location, the guidewire is or can be withdrawn. The physician then proceeds with the protocol of the procedure. A specific but non-limiting example of the above is the placement of a multi-lumen catheter into the internal jugular vein for intraveneous delivery of medications. The physician achieves venous access with a percutaneous introducer needle which penetrates the surrounding tissue and vessel wall as it enters the vessel lumen. The guidewire is inserted through the introducer needle and advanced to the internal jugular vein. The needle is withdrawn over the guidewire and placed on the sterile field, i.e., the sterile area surrounding and adjacent to the site of the medical procedure. A dilating sheath is inserted over the guidewire and advanced through the skin to enlarge the percutaneous opening. The dilating sheath is withdrawn over the guidewire and placed in the sterile field. The multi-lumen catheter is then slid over the guidewire by means of one of its lumens and advanced to the desired location. Once the catheter reaches the desired position within the vessel, the guidewire is withdrawn and placed on the sterile field for possible future use.

Depending upon the nature and complexity of the procedure, the physician may need or may choose to reinsert or use a number of additional other diagnostic, interventional, or therapeutic devices during the procedure. For example, fluoroscopic imaging may disclose the catheter to be incorrectly positioned. In that instance, the physician may choose to reinsert the guidewire to provide support to the catheter as the catheter is withdrawn or advanced to the correct position. Reinsertion of such other medical devices will necessitate reinsertion of the guidewire into the vasculature or to some other desired anatomical site. Numerous other medical procedures requiring guidewire reinsertion will be known to one skilled in this art. Thus, the guidewire must be readily available for use and must maintain its sterility throughout what may be a lengthy procedure.

The devices utilized during a procedure (including the guidewire), are laid out on a sterile field to be readily accessible to the physician throughout the procedure. The sterile field may include a tray, a draped table, or a draped portion of the patient's body. Therefore, the sterile field may be limited in space and sometimes may not be level, but rather, uneven or tilted. For example, as a preventative measure for reducing the likelihood of introducing an air embolism during a central venous access procedure, the patient table is commonly tilted with the patient's head angled downward toward the floor.

As presently commercially available, a guidewire's unpackaged shape is similar to a linear spring ranging in length from 30 centimeters to 300 centimeters or more. The guidewire is usually packaged in a circular carrier known as a dispenser, which has been discussed in numerous United States patents including U.S. Pat. Nos. 5,443,081 and 5,279,573 both issued to James J. Klosterman. Once removed from the dispenser, the guidewire returns to its straight, substantially linear form. Because of the linear form and circular cross section of the guidewire, it may inadvertently become displaced from the sterile field by rolling or falling off. Additionally, its tendency to be linear may result in contact with a non-sterile surface outside of the limited sterile field such as a portion of the patient's body, or a portion of the physician's body or a contaminated object. In those instances where the guidewire is displaced from the sterile field and has become contaminated, it is necessary for the guidewire to be replaced with a second, sterile guidewire. Replacement of the guidewire because of loss of sterility is disruptive, inefficiently time consuming, and increases the cost of the procedure.

At least two approaches have been taken to reduce the likelihood that a guidewire will become contaminated by inadvertent contact or displacement from the sterile field. One approach is to reinsert the guidewire into its sterile dispenser, mentioned above, as it is partially or wholly withdrawn from the patient. While this approach is effective in protecting the wire from contamination, re-loading the guidewire into the dispenser and removing it therefrom for reuse requires additional time and may not be practical during a medical procedure.

A second approach of which the assignee of this application has become aware is to manufacture the guidewire from a material having a temperature dependent configuration , i.e., the configuration the guidewire tends to assume, is determined by the temperature to which the guidewire is exposed. Materials useable in this approach can be processed to have a tendency to coil at room temperature (e.g., 25° C.) outside the body and to uncoil, i.e., to become substantially linear, at body temperature (e.g., 37° C.) e.g., when it is reinserted into the body. As is well known in the medical device art, specific nickel titanium alloys (e.g., nitinol) can be processed to exhibit this behavior. This second approach has the significant drawback that the materials which are suitable for manufacturing guidewires and which exhibit a temperature dependent configuration are generally difficult to fabricate into conventional guidewires because they are resistant to conventional welding and brazing processes. Additionally, such temperature dependent materials tend to be more expensive than conventional metals such as medical grade stainless steel.

The present invention provides the physician with a means of efficiently, conveniently and cost effectively reducing the risk of inadvertent contamination of the guidewire during a medical procedure use and handling, without re-loading the guidewire into its dispenser or utilization of materials which exhibit temperature-dependent memory.

BRIEF SUMMARY OF THE INVENTION

Briefly, in one aspect, the present invention is an elongate guidewire comprising a guidewire body having coupled or connected distal, medial and proximal segments. At least a substantial part of at least one of the distal, medial or proximal guidewire segments has a substantially permanent disposition or pre-disposition to assume the configuration or shape of a helical coil. Put otherwise, a guidewire of this invention self-coils to a coiled, usually circular, configuration or arrangement. In a preferred embodiment, substantially the entire guidewire body has a substantially permanent predisposition to coil. In yet a further preferred embodiment, the guidewire comprises metal which does not exhibit temperature dependent memory, especially including substantially conventional ferric metal such as medical grade stainless steel (e.g., 304 stainless steel).

The term "guidewire" as used herein is to be broadly construed to mean essentially any wire-like structure of dimension and length which is intended to assist in the placement of a catheter or other medical device at a site of medical interest. (Percutaneous procedures in which placement of a catheter or other device through the skin is contemplated, are a preferred category of medical procedures in which guidewire are used.) Guidewires herein is intended to include but is not limited to what is usually referred to as a guidewire, a main wire, introducer guidewires, diagnostic, therapeutic or interventional guidewires, wire guides, and spring guidewires, but also includes exchange guidewires and extension wires. Dimensions of guidewires to which the present invention applies falls in the range of about 0.010 in. to about 0.065 in. in diameter and about 30 cm to about 300 cm (or more) in length. Without limiting the generality of the foregoing, peripheral, cerebral (including neuro-interventional), cardiovascular (including coronary) guidewires or wire guides are within the contemplation of this definition. Guidewires of the present invention may include structure (e.g., on their extreme proximal segment) which permits them to be extended during a procedure by connection to a second (extension wire) guidewire. Guidewires of this invention may be coated or treated with various polymers or other compounds to change their handling or performance characteristics such as to increase lubricity, or to reduce thrombogenicity. Guidewires of the invention may also be uncoated.

Guidewires of the present invention, are required to have in at least some substantial portion of the body thereof a substantially "permanent" disposition or predisposition to coil. By this terminology it is intended that the guidewire, especially a substantial portion thereof, will have a substantially permanent, non-transitory, i.e., neither time nor temperature dependent, tendency or predisposition to maintain itself, or to return to (if it has been uncoiled) a coiled, usually circular, configuration. A substantially permanent predisposition to coil should not be narrowly construed to mean predisposition to return to precisely the same coiled configuration as was assumed before uncoiling. Coiling and uncoiling a guidewire of this invention, e.g., in the performance of multiple catheter exchanges, may change the precise coiled configuration to which the guidewire returns when it recoils. Such minor changes in the coil configuration (especially those associated with the use of guidewire of this invention) are intended to be within the definition of a substantially permanent predisposition to coil. As is described in greater detail below, a permanent predisposition to coil can be imparted to relatively conventional metals such as stainless steel. To obtain various other performance characteristics, e.g., radiopacity, guidewire components may be fabricated from alloys of platinum, gold, tantalum, nickel, titanium, or cobalt. Guidewires of this invention also may be fabricated from nonmetallic, polymer materials, assuming such materials display a permanent disposition or predisposition to assume a coiled configuration in accordance with this invention.

BRIEF DESCRIPTION OF THE DRAWINGS

The present invention will now be discussed in detail, the understanding of which will be enhanced by reference to the attached drawings wherein like numerals are used to refer to like features and wherein:

FIG. 2 is a detailed, partially sectional view of one embodiment of the present invention;

FIGS. 5 and 6 illustrate coiled guidewire carriers.

FIGS. 7–11 are schematic, perspective illustrations of tooling used to impart a permanent predisposition to coil to guidewires of the present invention.

DETAILED DESCRIPTION OF THE INVENTION

The invention will now be described with reference to the drawings noted above and the attached claims. The description of the present invention will focus upon its application to medical guidewires as that term is ordinarily understood in this art. However, the invention is not intended to be limited to medical guidewires as discussed herein and should be construed in accordance with the above definitions.

Figure 1A:
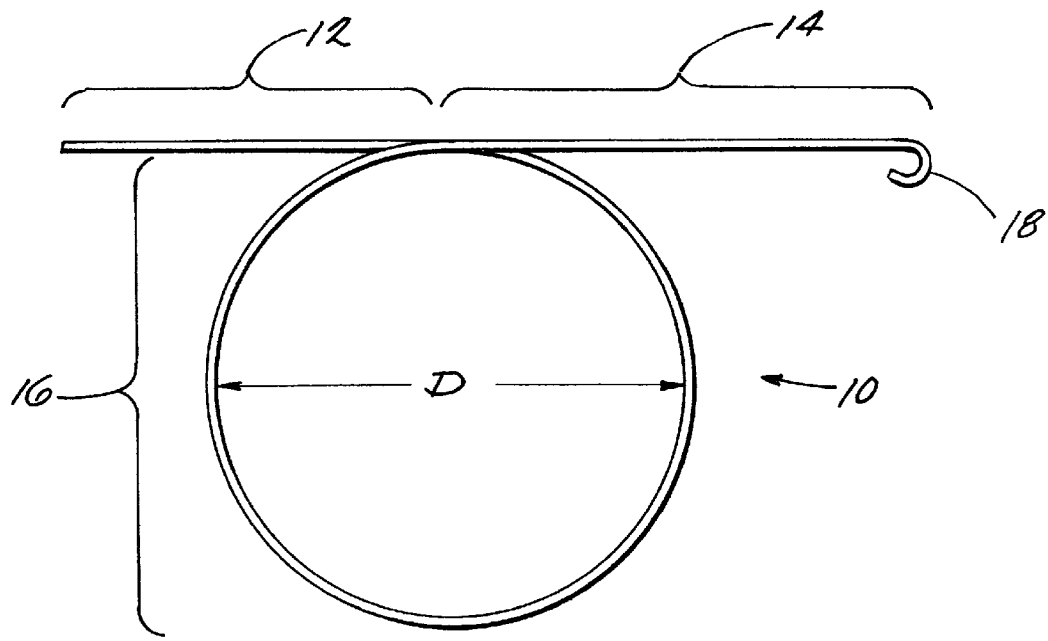
FIGS. 1A and 1B are perspective, schematic views of guidewires of the present invention.
Figure 1B:
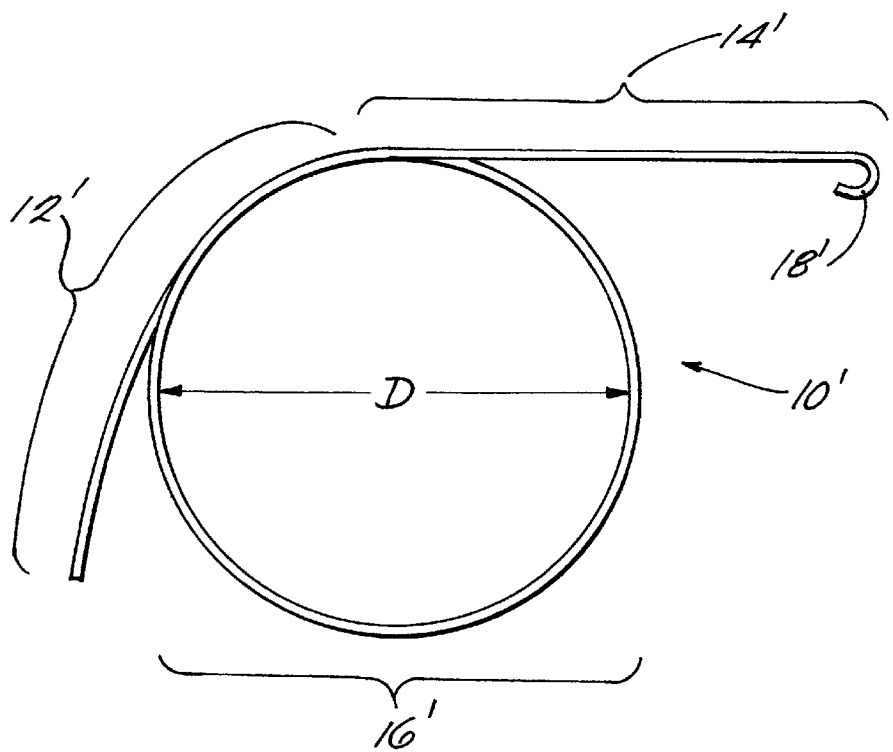

FIGS. 1A and 1B are schematic depictions of guidewires 10, 10' of the present invention shown in their coiled configuration. Guidewires 10, 10' comprise a guidewire body having a connected or coupled proximal segment 12, 12', a distal segment 14, 14', and a permanently coiled medial segment 16, 16'. The terminology proximal, medial, and distal, as it is used with reference to guidewire structure, will be well understood by one skilled in this art to mean structures of the wire as determined from the user's perspective. More specifically, the distal segment of a wire of this invention generally means that portion of the guidewire which first enters a patient's anatomy when the device is utilized. The distal segment of any particular guidewire tends to be more flexible than the rest of the guidewire. This distal segment of a guidewire also may be bent to have a "J" configuration as viewed from the side. The medial segment of the guidewire is generally any portion of the wire between the distal segment and the proximal segment. The proximal segment of the wire is generally that portion of the wire where much of the manual manipulation of the guidewire occurs and which does not usually enter the patient's anatomy during a medical procedure. In any particularly instance, designation of a guidewire length into distal, medial, and proximal segments is not particularly critical as the present invention may be applied to any, all, or a combination of those guidewire body segments. Generally speaking, the medial segment of a guidewire of this invention will comprise a majority of the length of the guidewire body and will be imparted with a predisposition to assume a coiled configuration in accordiance with this invention. In this general practice of the present invention, a greater percentage of the guidewire body is coiled, thereby imparting control and the advantageous handling characteristics of this invention to more of the guidewire body.

In the embodiments of FIGS. 1A and 1B, the distal-most portion of the guidewire has a "J" configuration or distal tip 18, 18' which tends to make the extreme distal end of distal segment 14, 14' of the wire atraumatic to the patient's vessels, tissue and other body structures with which it comes in contact during use. While a "J" distal guidewire tip configuration is illustrated with respect to this invention, a straight distal tip, or merely a bent distal tip are equally within its scope. As is shown in FIG. 1A, the proximal segment 12 of wire 10 is substantially straight having no disposition to coil. Proximal coil segment 12', as shown in FIG. 1B has a slightly curved configuration, albeit with a radius of curvature larger than that of medial segment 16'. Proximal segments 12, 12' may be designed to have various configurations, including bent, slightly to extremely curved or circular, depending upon the intended use for the wire. Proximal segment 12, 12' and distal segment 14, 14' may be imparted with a tendency to assume a configuration in which their respective radii of curvature are substantially the same as that of medial segment 16, 16'. In that embodiment, the only deviation from the curved configuration throughout the entire length of guidewires 10 or 10' would be the extreme distal tip 18, 18'. Generally speaking, at least some part of one or both distal segments 14, 14' and proximal segments 12, 12' will be substantially straight (or will be made to be straightened during the procedure as is described below) so as to make easier the advancement of guidewire 10, 10' through an introducer needle or other entry device. The straight length of segments 12, 12' and 14, 14' (which may be the same or different) generally ranges from about 5 cm to about 30 cm.

Medial segment 16, 16' of guidewires 10, 10' is shown to be curved, or more precisely circular in FIGS. 1A and 1B. Elliptical, flattened elliptical, or various other permanent configurations may be imparted to the wire in accordance with this invention. One skilled in this art will appreciate that essentially any permanent configuration which tends to contain or manage all or substantially all of the sometimes cumbersome length of the guidewire body to make it more controllable during a medical procedure (and also to reduce the likelihood that the device will leave the sterile field) is within the contemplation of this invention. It is also to be understood that guidewire proximal segment 12, 12' and distal segment 14, 14' are generally much shorter in length that medial segment 16. For example, the distal and proximal segments 12, 12' and 14, 14', respectively, of a guidewire of this invention may fall in the range of 5 cm to 30 cm while the length of the entire guidewire may fall in the range of 30 cm to 300 cm or more. Thus, while medial segment 16, 16' is shown to comprise a single coil in FIGS. 1A and 1B, it is to be understood that medial segment 16, 16' may comprise a plurality of coils depending upon overall guidewire length. Generally speaking, whether medial segment 16, 16' comprises a single permanent coil, or a plurality of permanent coils, the preferred coil diameter ("D") in FIGS. 1A and 1B) falls in the range of about 2½ inches (10 cm) to about 10 inches (25 cm). Using a predispositioned coil diameter ("D") in the range discussed above in conjunction with the indicated ranges for guidewire length and cross-sectional diameter, the guidewire will have a permanent disposition to coil when withdrawn from the patient without having an excessive tendency to do so, i.e., so as to cause injury while in the patient. In essence, the patient's anatomical structure will overcome the tendency of the guidewire to self-coil, permitting the guidewire to be inserted and withdrawn without unwanted deflection. The guidewire then returns to its coiled configuration as it is withdrawn from the constraints of the patient's anatomical structure.

It is to be understood that the preferred practice of the present invention is to impart a substantially permanent coil predisposition or self-coiling disposition to the medial segment of a guidewire. Generally speaking, this means that all or substantially all of the medial segment of the wire will be imparted with a predisposition to assume a curved structure or substantially circular configuration. Depending upon the intended application, the predisposition to curve may be imparted to the medial segment, either of the proximal and distal segments, both of the proximal and distal segments or all of the distal, medial, or proximal guidewire segments.

At least two processes have been identified for permanently imparting such predisposition to the various guidewire segments, i.e., cold forming and hot forming. The particular process chosen may, in part, be determined by the structural configuration of the guidewire. Other processes may occur to one skilled in this art. A brief description of a preferred guidewire of this invention may assist in the comprehension of the fabrication processes described below.

The preferred guidewire structure for application of the present invention is an assembly of a coil component and a core component as is shown in FIG. 2. In FIG. 2, there is shown a guidewire 30 which comprises a core component such as core wire 32 (sometimes referred to as a mandril in prior art patents) and a coil component such as coil wire 34. Coil wire 34 is shown partially cut-away and in section to permit discussion of the guidewire interior structure. Guidewire 30 has a proximal segment 31, and a distal segment 33. Guidewire 30 of FIG. 2 is shown in segments to permit the various structural features to be discussed. It is to be understood that a medial segment having a substantially permanent predisposition to assume a curved or coiled configuration would be located between proximal segment 31 and distal segment 33. In FIG. 2 coil wire 34 is disposed around essentially the entire length of core wire 32. Coil wire 34 is closely wound meaning that individual coils 36, 38 are in contact with each other. Coil wire 34 could be space wound, meaning that individual coils thereof would not be in contact each other and would have air space therebetween. Coil wire 34 also could be partially space wound and partially closely wound (shown in FIG. 3). Coil wire 34 is attached to core wire 32 at its most distal and proximal ends by distal weld 40 and proximal weld 42. Welds 40 and 42 are rounded or atraumatic so as to reduce possible damage to the structure of any cooperating device or any tissue with which they may come into contact. Braze, solder, or adhesives are other means for attaching the coil and core components.

Figure 3:
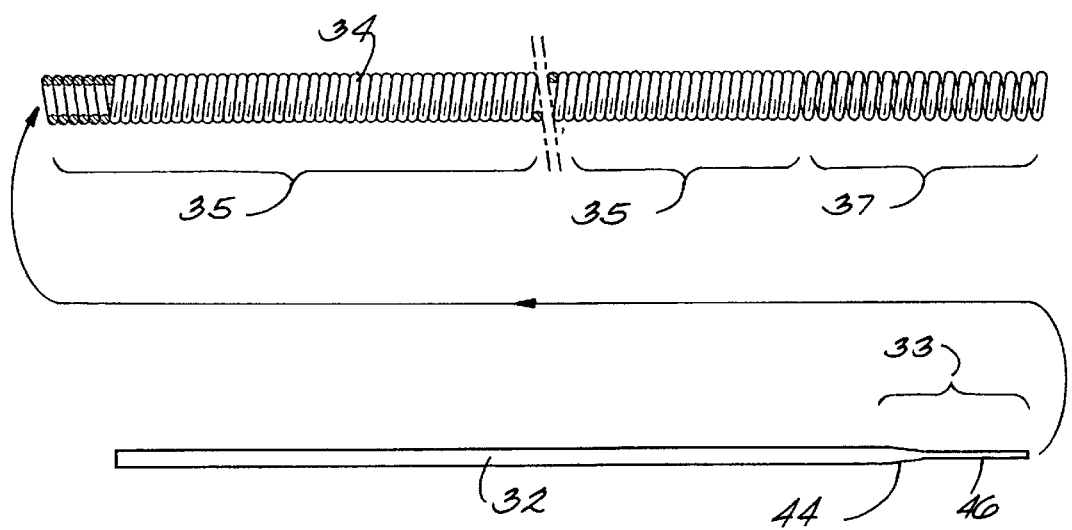
FIG. 3 is an exploded view of an assembly step in a method of this invention.

FIG. 3 illustrates the individual coil wire 34 and core wire 32 components prior to assembly. It is to be noted that the term wire as used in this context includes a linear and coiled wire segments. Multifilar guidewire structures comprising a plurality of wound coil structures, are also within this definition. Distal segment 33 of core wire 32 has a first tapered section 44 and is coupled to a reduced diameter distal portion 46. Tapered section 44 and reduced diameter portion 46 provide enhanced flexibility to the distal segment of the guidewire. Such structures may be used on either or both the distal and proximal ends of a guidewire, especially is the guidewire is designed so that either end of the guidewire may be inserted into the patient's anatomy. Wire core 32 may also include a flattened extreme distal section (or an extreme proximal section) on either or both of its ends to impart flexibility thereto. For illustrative purposes only (i.e., the assembled structure of the FIGs. do not have a partially space wound coil) coil wire 34 is shown to have a tightly wound portion 35 and a space wound portion 37.

Figure 4:
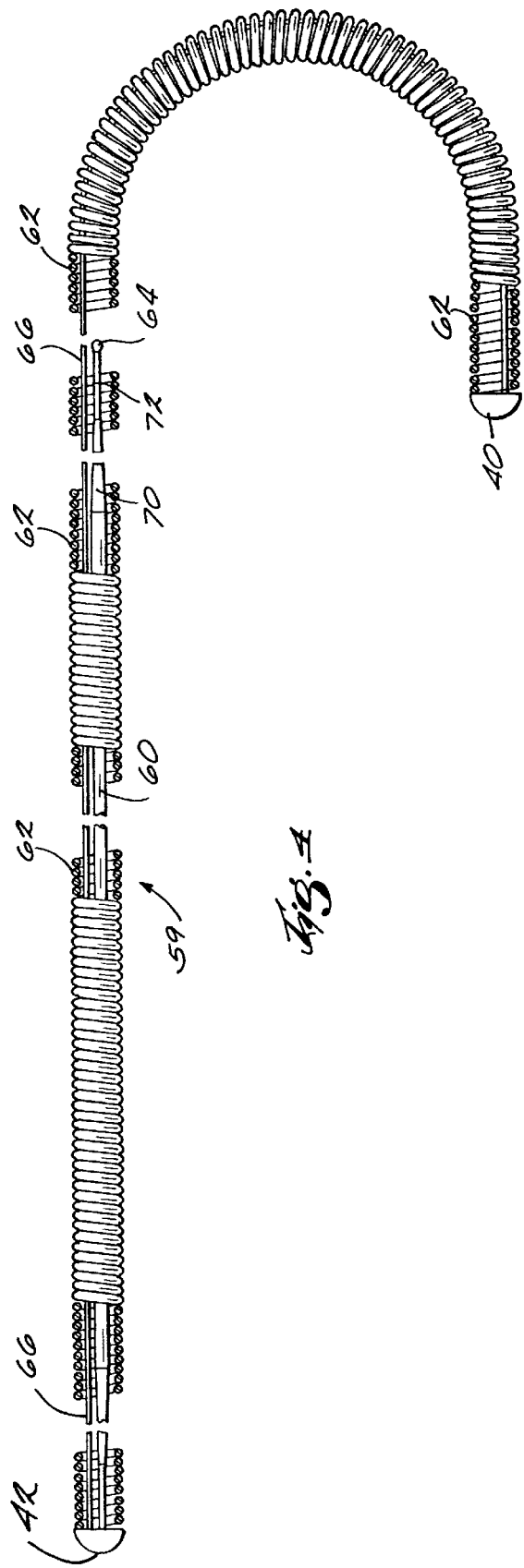
FIG. 4 is a detailed, partially sectional view of a second embodiment of this invention.

FIG. 4 shows a further embodiment of a guidewire configuration 59 with which the present invention may be used. As with FIG. 3, the coiled medial segment has been deleted but should be understood to be implicitly present. In FIG. 4, there is shown a core wire 60, and a wire coil 62 in which core wire 60 terminates short of the distal end 40 of the wire coil at distal ball weld 64. Wire core 60 has distal ball weld 64 which reduces the likelihood that core wire 60 will project from between the coils of coil wire 62. Running the entire length of guidewire 59 is safety wire 66. Safety wire 66 is attached to wire coil 62 at distal weld 40 and proximal weld 42. This embodiment of the invention would be used where an especially flexible or "floppy" distal tip guidewire is required. As in the embodiment of FIG. 2, core wire 60 has a first tapered segment 70 leading to a reduced diameter segment 72.

FIGS. 5 and 6, illustrate further embodiments of the present invention in which guidewires within its scope are contained within single 20 and multiple coil 22 guidewire carriers. Also shown in FIGS. 5 and 6 is the utilization of a "J" straightener 24 which, in accordance with known practice, temporarily straightens the distal "J" tip to permit the tip to be inserted into the vasculature, e.g., through an introducer wire. See, e.g., U.S. Pat. No. 4,650,472. While the present invention has been discussed in conjunction with the utilization of guidewire carriers, one advantage of this invention is that it provides the option to use a guidewire without the need for a guidewire carrier. The permanent predisposition of a guidewire to coil, in accordance with this invention, provides many of the transportation, handling, and packaging functions of a guidewire carrier and, depending upon user preference, may be substituted therefor. In this manner the expense of the guidewire carrier itself and of its environmentally acceptable disposal may be reduced or eliminated.

In a cold rolling process, the segment of the guidewire into which a permanent coiling predisposition is to be imparted is passed between a series of rollers at room temperature, after the wire core and coil wire have been attached to each other, e.g., at welds 40 and 42. In one version of a cold rolling process a series of 4 rollers as is shown in FIGS. 7–11 is used.

In FIGS. 7–11 (specifically FIG. 7) there is shown a primary bend pin or roller 50, control rollers 52 and 54, and a bend backroller or sizing roller 56. Roller direction is shown by arrows 55. In each of rollers 50 and 56 there is a groove or channel 57 which is sized and aligned with the other rollers to receive a guidewire (not shown). It is preferred that at least one of bend roller 50, control rollers 52 and 54 or bend backroller 56 have a guidewire-sized channel or groove to retain the guidewire between the rollers in the bending process. A substantially permanent predisposition to assume a coiled configuration is imparted to a guidewire (in this example, the medial segment) in the following manner.

Figure 8:
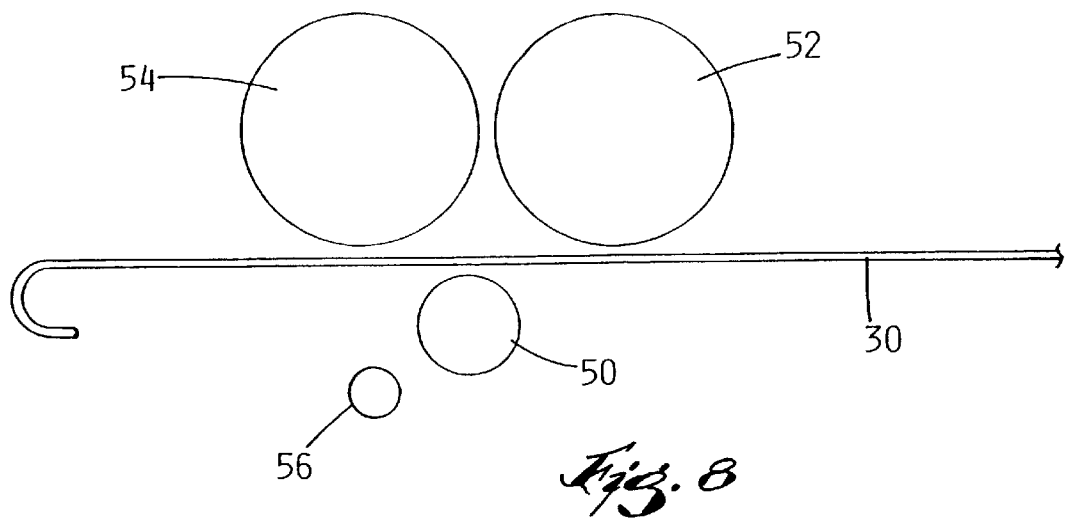
Figure 9:
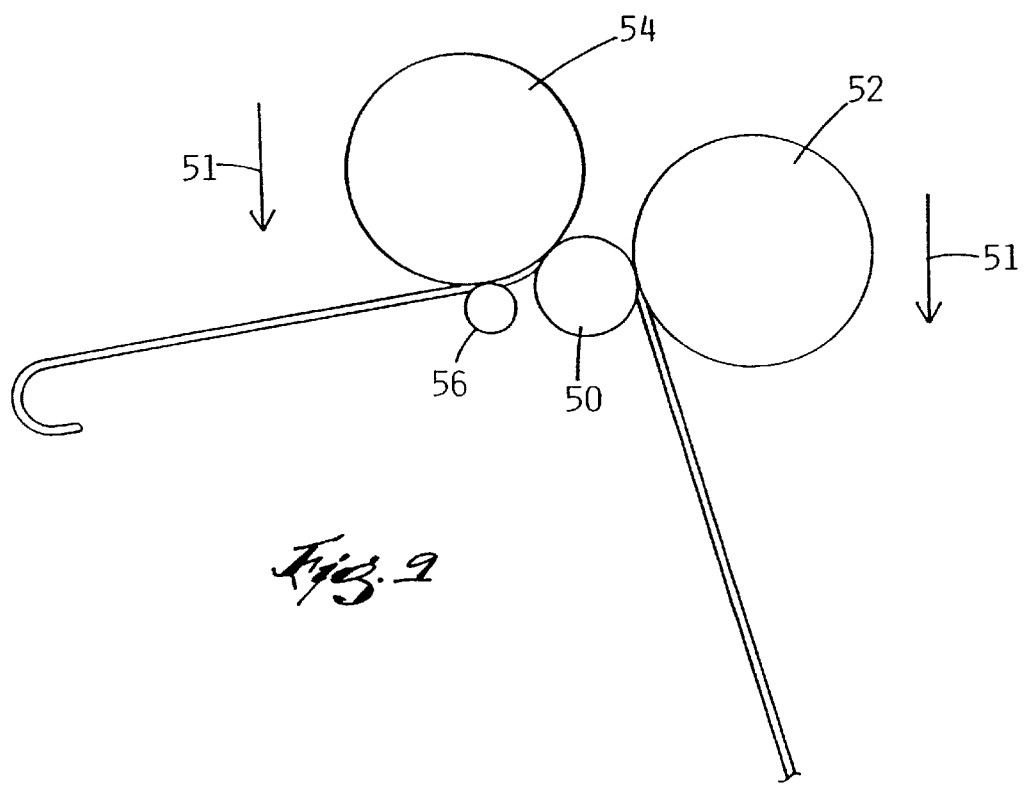
Figure 10:
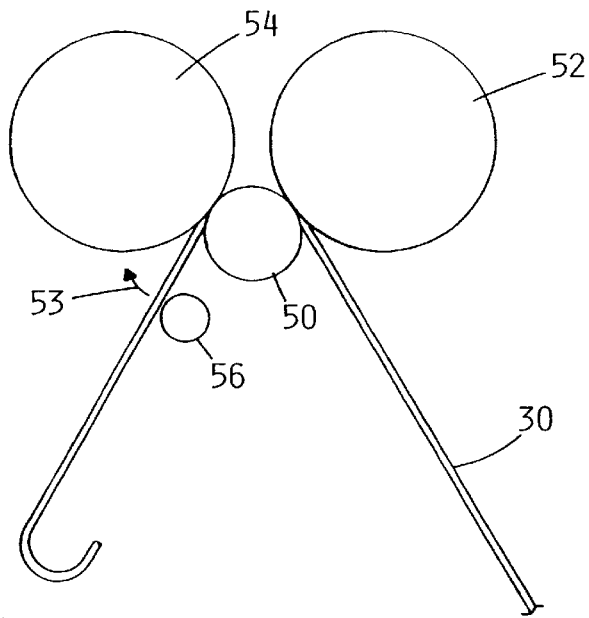
Figure 11:
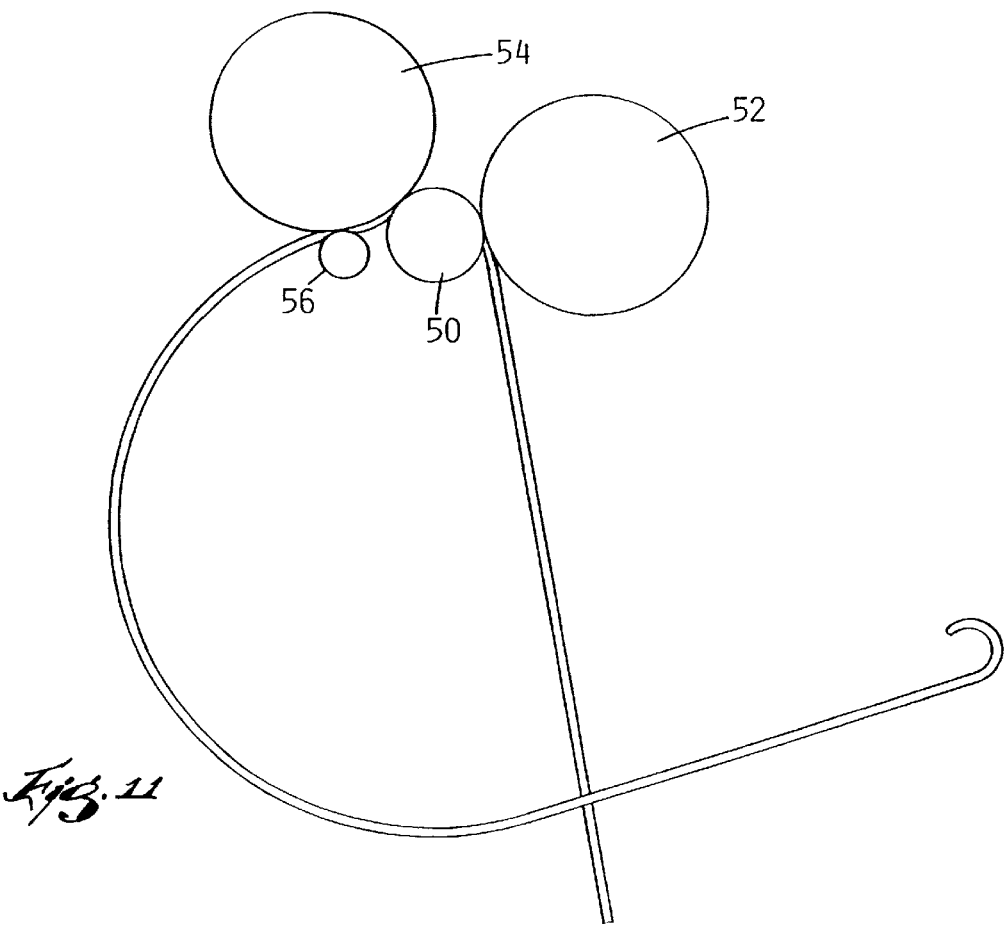

Referring to the top view of FIG. 8, the medial segment of guidewire 30 is placed between control rollers 52, 54 and bend roller 50 in channel 57 (not shown). Control rollers 52, 54 then are moved toward bend roller 50 in the direction of arrows 51 (FIG. 9) to start the bending process. Control rollers 52, 54 are rotated clockwise with main bend roller 50 holding guidewire 30 therebetween and rotating counter-clockwise to impart an initial bend to the guidewire (FIG. 10). Generally speaking, guidewire 30 will be overbent during this initial step to ensure that the guidewire, will return to the desired shape or degree of curvature and after procedural use and handling. Sizing or bendback roller 56 may then be moved into position in the direction shown by arrows 53 as is shown in FIGS. 10 and 11 to modify the bend and therefor the extent of the coiling predisposition imparted to the guidewire. One skilled in the art of bending wire will appreciate that the relative locations and relative diameters of rollers 50,52, and 54 may be changed to impart particular curvilinear predispositions (i.e., coil diameters or coil memory) to produce a self-coiling guidewire structure in accordance with this invention. Adjustment of the roller diameters and of the number of times the guidewire is rolled therebetween also will determine the aggressiveness or resistance to uncoiling the guidewire exhibits.

In a heat forming process, wire core 32 is heated to a temperature in the range of about 500° F. to about 1200° F. for a minimum time period of from about 15 minutes while it is maintained in a looped or coiled configuration. Heating the wire core to a temperature in the indicated range while maintaining it in a coiled configuration tends to relieve any stresses in the metal and, upon cooling to room temperature, produces a permanently coiled wire core in accordance with this invention. Thereafter, the coiled wire core is attached to the coil wire by inserting the wire core into the coiled wire and joining the distal and proximal ends of wire core and the coil wire. The coil wire, being substantially more flexible than the wire core tends to assume the same coiled configuration as the wire core. In this later, heat forming process, "J" guidewire tip configurations are generally imparted to the distal end of the guidewire between attachment (e.g., by welding) of the distal and proximal ends of the guidewire structure. This permits the length relationship between the coil and the core to be more precise.

The embodiment of the present invention shown in FIGS. 2 and 4 have an optional feature, in that the "J" tip is finger-straightenable. Finger-straightenability is imparted to the "J" distal tip by manufacturing coil 62 from a wire diameter which is typically 0.001" smaller than convention coil wire size. Additionally, safety wire 66 (FIG. 4) or core wire 60 (FIG. 4) are downsized from conventional designs (e.g., by a reduction in cross-sectional thickness of at least 15%) to create less resistance to opening of the J-shaped tip. Reference is now made to FIGS. 12A–12D in which finger straightenability is illustrated.

Figure 12A:
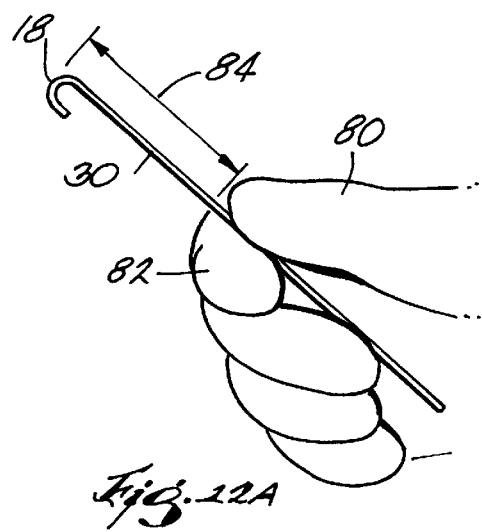
FIGS. 12A–12D illustrate the finger-straightenable optional feature of the present invention.
Figure 12B:
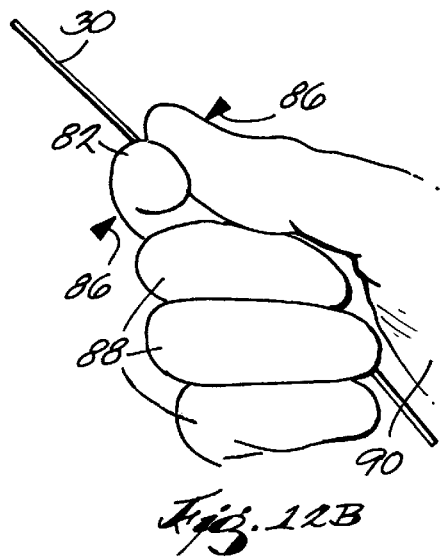
Figure 12C:
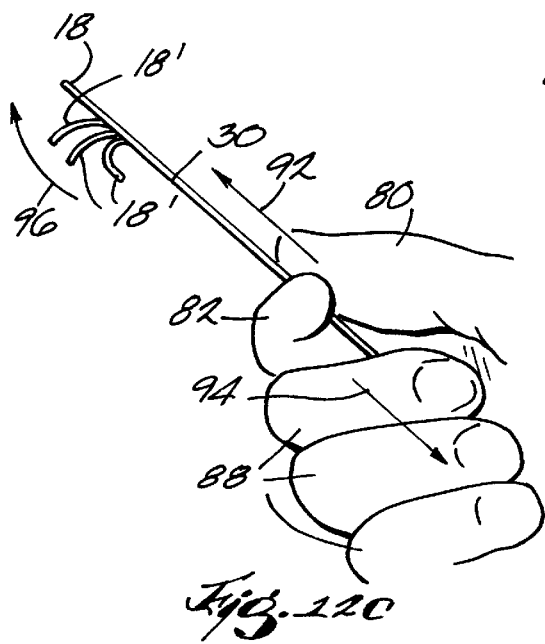
Figure 12D:
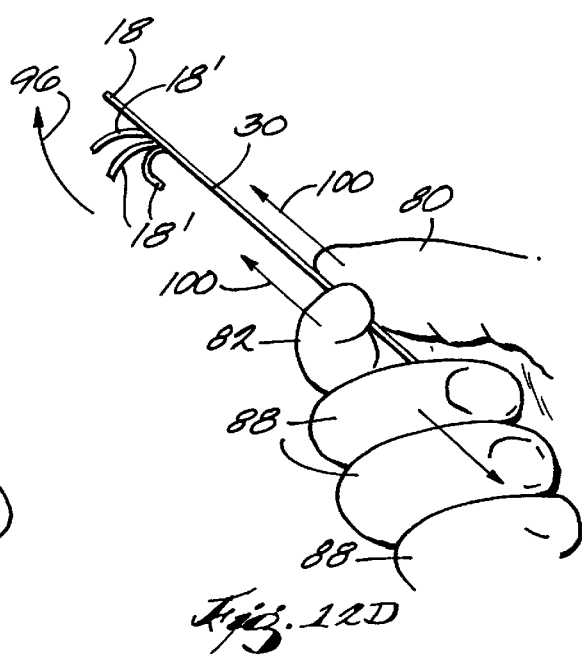

FIG. 12A illustrates a guidewire 30 such as that of FIG. 2, above, held between the gloved thumb 80 and forefinger 82 of the guidewire user. Arrow 84 indicates that the guidewire 30 is gripped approximately 5–6 cm from its distal "J" tip 18. In FIG. 12B, triangles 86 indicate that the guidewire is held securely between the thumb 80 and forefinger 82 while wrapping fingers 88 around guidewire 30 pressing guidewire 30 against the user's palm 90. As is shown in FIG. 12C, forward pressure (indicated by arrow 92) is applied with the thumb 80 while simultaneously pulling downward with the remaining fingers 82,86 (indicated by arrow 94) until the guidewire "J" distal tip 18 gently straightens (as is shown by arrow 96 and the phantom "J" tip, 18'.) Alternatively, as is shown in FIG. 12D., forward pressure is applied by both the thumb 80 and forefinger 82 (in the direction of arrows 100) while holding guidewire 30 with the remaining fingers 88. In like manner, the guidewire "J" distal tip 18', 18 is straightened. After finger-straightening the "J" distal tip as illustrated, the guidewire than can easily be introduced into an introducer needle, a cannula, or a catheter or other structure without the assistance of a separate "J" straightening device.

Materials of which the wire core and coil wire may be made are substantially conventional. Stainless steel, e.g., 304 stainless steel, nickel and nickel alloys, e.g., MP-35N, cobalt alloys, and various other ferrous metals commonly used in guidewire fabrication may be used. Radiopaque alloys such as platinum and titanium may be used to fabricate, in whole or in part, either or both of the wire core and the coil wire or various other structural components. Etches may be applied to the guidewire body. As is noted above, multifilar construction using any of the above materials is also within the contemplation of the present invention.

The above-described preferred guidewire structure is used substantially without a coating of any sort. Obviously, various coatings could be imparted to the wire core, the coil wire, or both without departing from the scope of the present invention. PTFE and hydrophilic coatings are commonly used to impart desirable handling characteristics to a guidewire. Such coatings are within the scope of the present invention.

The present invention has been particularly described with respect to the utilization of guidewires, primarily to obtain percutaneous vascular access. Non-vascular access applications are also within the scope of the present invention. For example, a device of the present invention may be used to assist in the performance of percutaneous nephrostomy, biliary and abscess drainage and other gastrointestinal and genitourinary procedures.

In one application, then, a guidewire of this invention is removed from its guidewire carrier, examples of which are shown in FIGS. 5 and 6 by withdrawing it therefrom. Upon removal, the guidewire returns to its substantially permanently coiled disposition. The user then inserts the extreme distal end, e.g., the "J" tip, as described above into the chosen percutaneous access device after it is straightened by means of a "J" straightener or by utilization of finger straightenability. The guidewire then is steered to the previously chosen site of medical interest by uncoiling it while inserting it into the patient. Using the coil diameter above-discussed (i.d., the "D" dimensions) in conjunction with the indicated guidewire length and diameters, the guidewire will not have an excessive tendency to coil while in the patient. In essence, the user's hands and the patient's anatomical structure overcome the tendency of the guidewire to self-coil and permit the guidewire to be inserted. When the guidewire is withdrawn from the patient, e.g., to exchange catheters, the guidewire returns to its coiled configuration as it is withdrawn.

What is claimed is:

1. An elongate, guidewire comprising a guidewire body having coupled distal, medial and proximal segments, wherein at least a substantial portion of at least one of said segments of the guidewire has a substantially permanent disposition to assume a coiled configuration whereby said segment has neither a time nor temperature dependent tendency to return to a non-coiled configuration.

2. A guidewire according to claim 1 wherein the segment having the disposition to assume a coiled configuration is the medial segment.

3. A guidewire according to claim 2 wherein substantially the entire medial segment has a disposition to assume a coiled configuration.

4. A guidewire according to claim 1 wherein the guidewire comprises a wire core and a coil wire.

5. A guidewire according to claim 4 wherein the wire core comprises stainless steel and the coil wire comprises an alloy of platinum.

6. A guidewire according to claim 1 wherein at least a substantial portion of the distal segment has a diameter which is less than that of the medial segment.

7. A guidewire according to claim 1 wherein the guidewire comprises a polymeric material.

8. A guidewire according to claim 1 wherein the guidewire comprises a core wire having distal and proximal ends, a coil wire having distal and proximal ends, and a safety wire, the proximal ends of the core wire and coil wire being essentially coterminous and attached to each other, the core wire terminating short of the coil wire distal end, and the safety wire is attached to the distal and proximal ends of the coil wire.

9. An elongate, guidewire comprising a guidewire body having coupled distal, medial and proximal segments, wherein at least a substantial portion of at least one of said segments of the guidewire has a substantially permanent disposition to assume a coiled configuration and said guidewire body comprises medical grade stainless steel whereby said segment has neither a time nor temperature dependent tendency to return to a non-coiled configuration.

10. A guidewire according to claim 9, wherein the segment having the disposition to assume a coiled configuration is the medial segment.

11. A guidewire according to claim 9, wherein substantially the entire medial segment has a disposition to assume a coiled configuration.

12. A guidewire according to claim 9, wherein the guidewire comprises a wire core and a coil wire.

13. A guidewire according to claim 9, wherein the wire core comprises stainless steel and the coil wire comprises an alloy of platinum.

14. A guidewire according to claim 9, wherein at least a substantial portion of the guidewire body distal segment has a diameter which is less than that of the guidewire body medial segment.

15. A guidewire according to claim 9, wherein the guidewire comprises a core wire having a distal and proximal end, a coil wire having a distal and proximal end, the proximal ends of the core wire and coils wire being essentially coterminous and attached to each other, the core wire terminating short of the coil wire distal end, and a safety wire attached to the distal and proximal ends of the coil wire.

* * * * *